United States Patent
Stephens et al.

(10) Patent No.: US 10,228,311 B2
(45) Date of Patent: Mar. 12, 2019

(54) AUTOMATED LEAN METHODS IN ANATOMICAL PATHOLOGY

(71) Applicant: Ventana Medical Systems, Inc., Tucson, AZ (US)

(72) Inventors: Randy Stephens, Honey Grove, TX (US); Brian H. Kram, Tucson, AZ (US)

(73) Assignee: VENTANA MEDICAL SYSTEMS, INC, Tucson, AZ (US)

( * ) Notice: Subject to any disclaimer, the term of this patent is extended or adjusted under 35 U.S.C. 154(b) by 32 days.

(21) Appl. No.: 15/295,210

(22) Filed: Oct. 17, 2016

(65) Prior Publication Data

US 2017/0030810 A1    Feb. 2, 2017

Related U.S. Application Data

(63) Continuation of application No. 11/639,586, filed on Dec. 15, 2006, now abandoned.
(Continued)

(51) Int. Cl.
*G01N 1/31* (2006.01)
*G01N 1/28* (2006.01)
(Continued)

(52) U.S. Cl.
CPC ............ *G01N 1/312* (2013.01); *G01N 1/06* (2013.01); *G01N 1/286* (2013.01);
(Continued)

(58) Field of Classification Search
None
See application file for complete search history.

(56) References Cited

U.S. PATENT DOCUMENTS 5,614,415 A    3/1997    Markin
5,690,892 A    11/1997    Babler et al.
(Continued)

FOREIGN PATENT DOCUMENTS

AU    2012209030 A1    8/2012
CA    2688530    12/2008
(Continued)

OTHER PUBLICATIONS

Japanese Office Action dated Feb. 19, 2013.
Japanese Office Action dated Sep. 20, 2011.

*Primary Examiner* — Kathryn Wright
(74) *Attorney, Agent, or Firm* — Muirhead and Saturnelli, LLC

(57) ABSTRACT

An embodiment of the method of the invention is a method of automating information flow in a laboratory performing tissue staining comprising positioning a networked label printer adjacent to a cutting station, the printer configured to access patient data directly or indirectly from the hospital LIS, the printer being configured with a data element scanner in electronic communication with said printer; inputting data from a tissue cassette-associated data element at said printer, whereby inputting data comprises reading the data from the cassette-associated data element and uploading the cassette data to the LIS; identifying the corresponding test protocol identifier and then downloading the test protocol data to the printer; printing information on labels corresponding to each test specified in the LIS for the patient; attaching a single label to each slide; and cutting a tissue section for each labeled slide and mounting the section on the slide.

14 Claims, 5 Drawing Sheets

Related U.S. Application Data

(60) Provisional application No. 60/751,807, filed on Dec. 19, 2005.

(51) Int. Cl.
   *G01N 1/06* (2006.01)
   *G01N 35/00* (2006.01)

(52) U.S. Cl.
   CPC ............ *G01N 35/00722* (2013.01); *G01N 2001/2873* (2013.01); *G01N 2035/00861* (2013.01); *G01N 2035/00881* (2013.01); *Y10T 436/11* (2015.01)

(56) References Cited

U.S. PATENT DOCUMENTS

| | | | |
|---|---|---|---|
| 5,814,276 | A | 9/1998 | Riggs |
| 5,854,075 | A | 12/1998 | Levine et al. |
| 5,961,923 | A | 10/1999 | Nova et al. |
| 5,985,670 | A | 11/1999 | Markin |
| 6,045,759 | A | 4/2000 | Ford et al. |
| 6,093,574 | A | 7/2000 | Druyer-Sanchez et al. |
| 6,562,299 | B1 | 5/2003 | Ostgaard et al. |
| 6,572,824 | B1 | 6/2003 | Ostgaard et al. |
| 6,581,012 | B1 | 6/2003 | Aryev et al. |
| 6,599,476 | B1 | 7/2003 | Watson et al. |
| 7,035,877 | B2 | 4/2006 | Markham et al. |
| 7,041,206 | B2 | 5/2006 | Gephart et al. |
| 7,226,788 | B2 | 6/2007 | De La Torre-Bueno |
| 7,357,298 | B2 | 4/2008 | Pokorny et al. |
| 7,382,258 | B2 | 6/2008 | Oldham et al. |
| 7,468,161 | B2 | 12/2008 | Reinhardt et al. |
| 7,562,025 | B2 | 7/2009 | Mallett et al. |
| 7,584,019 | B2 | 9/2009 | Feingold et al. |
| 7,588,728 | B2 | 9/2009 | Clark et al. |
| 7,593,787 | B2 | 9/2009 | Feingold et al. |
| 7,603,201 | B2 | 10/2009 | Feingold et al. |
| 7,657,070 | B2 | 2/2010 | Lefebvre |
| 7,660,724 | B2 | 2/2010 | Mallett et al. |
| 7,664,656 | B2 | 2/2010 | Mallett et al. |
| 7,666,355 | B2 | 2/2010 | Alavie et al. |
| 7,678,331 | B2 | 3/2010 | Shanafelter |
| 7,688,207 | B2 | 3/2010 | Fritchie et al. |
| 7,745,204 | B1 | 6/2010 | Aidun et al. |
| 7,754,149 | B2 | 7/2010 | Sugiyama |
| 7,850,912 | B2 | 12/2010 | Favuzzi et al. |
| 7,860,727 | B2 | 12/2010 | Showalter et al. |
| 7,864,380 | B2 | 1/2011 | Descour et al. |
| 7,968,051 | B2 | 6/2011 | Oonuma |
| 7,996,172 | B2 | 8/2011 | Bauer et al. |
| 8,035,485 | B2 | 10/2011 | Fritchie |
| 8,062,591 | B2 | 11/2011 | Yamamoto |
| 8,609,023 | B1 | 12/2013 | Druyer-Sanchez et al. |
| 2003/0092186 | A1 | 5/2003 | Pressman et al. |
| 2003/0120633 | A1* | 6/2003 | Torre-Bueno .......... G16H 10/40 |
| 2004/0005245 | A1 | 1/2004 | Watson et al. |
| 2004/0253662 | A1 | 12/2004 | Heid et al. |
| 2005/0038676 | A1 | 2/2005 | Showalter et al. |
| 2005/0144044 | A1 | 6/2005 | Godschall et al. |
| 2005/0159982 | A1* | 7/2005 | Showalter ............ G06Q 10/00 705/2 |
| 2005/0235542 | A1 | 10/2005 | Metzner et al. |
| 2006/0088940 | A1 | 4/2006 | Feingold et al. |
| 2006/0105359 | A1 | 5/2006 | Favuzzi et al. |
| 2006/0148063 | A1 | 7/2006 | Fauzzi et al. |
| 2006/0155487 | A1 | 7/2006 | Yundt-Pacheco |
| 2006/0178776 | A1 | 8/2006 | Feingold et al. |
| 2006/0190185 | A1 | 8/2006 | Ford et al. |
| 2006/0210432 | A1 | 9/2006 | Victor |
| 2007/0005169 | A1 | 1/2007 | Röhnert et al. |
| 2007/0029342 | A1 | 2/2007 | Cross et al. |
| 2007/0053794 | A1 | 3/2007 | Perez et al. |
| 2007/0112804 | A1 | 5/2007 | DeSimas et al. |
| 2007/0159688 | A1 | 7/2007 | Descour et al. |
| 2007/0172100 | A1 | 7/2007 | Lefebvre |
| 2007/0196909 | A1 | 8/2007 | Showalter et al. |
| 2007/0207490 | A1 | 9/2007 | Benfield et al. |
| 2007/0208534 | A1 | 9/2007 | Benfield et al. |
| 2007/0217949 | A1 | 9/2007 | Mimura et al. |
| 2007/0224699 | A1 | 9/2007 | Gates |
| 2007/0245184 | A1 | 10/2007 | Benfield et al. |
| 2007/0254277 | A1 | 11/2007 | Scrabeck et al. |
| 2008/0006653 | A1 | 1/2008 | Dai et al. |
| 2008/0024301 | A1 | 1/2008 | Fritchie et al. |
| 2008/0220469 | A1 | 9/2008 | Heid et al. |
| 2008/0235055 | A1 | 9/2008 | Mattingly et al. |
| 2008/0307117 | A1 | 12/2008 | Muller-Cohn et al. |
| 2009/0155838 | A1 | 6/2009 | Hale |
| 2009/0177427 | A1 | 7/2009 | Bauer et al. |
| 2009/0254572 | A1 | 10/2009 | Redlich et al. |
| 2009/0291427 | A1 | 11/2009 | Muller-Cohn et al. |
| 2009/0298132 | A1 | 12/2009 | Muller-Cohn et al. |
| 2010/0009460 | A1 | 1/2010 | Clark et al. |
| 2010/0021352 | A1 | 1/2010 | Trueeb et al. |
| 2010/0063847 | A1 | 3/2010 | Eisenberg et al. |
| 2010/0070305 | A1 | 3/2010 | Eisenberg et al. |
| 2010/0113288 | A1 | 5/2010 | Adey et al. |
| 2010/0123551 | A1 | 5/2010 | Fritchie |
| 2010/0126286 | A1 | 5/2010 | Self et al. |
| 2010/0167334 | A1 | 7/2010 | Williamson, IV |
| 2010/0217620 | A1 | 8/2010 | Kippenhan et al. |
| 2011/0047092 | A1 | 2/2011 | Taylor |
| 2011/0115610 | A1 | 5/2011 | Hughes |

FOREIGN PATENT DOCUMENTS

| | | |
|---|---|---|
| CA | 2699386 | 3/2009 |
| CN | 2881785 Y | 3/2007 |
| GB | 2475835 A | 6/2011 |
| JP | 2003-279582 | 10/2003 |
| JP | 2003-329690 | 11/2003 |
| JP | 2010-217042 A | 9/2010 |
| WO | WO2001/94016 A1 | 12/2001 |
| WO | WO2003040697 | 10/2002 |
| WO | WO2004/074845 A2 | 9/2004 |
| WO | WO 2006/019392 A1 | 2/2006 |
| WO | WO 2007/123879 A2 | 11/2007 |
| WO | WO 2008/156566 A1 | 12/2008 |
| WO | WO 2011/063139 A1 | 5/2011 |

* cited by examiner

Figure 1 - Histology Process Map

PRIOR ART

AUTOMATED LEAN METHODS IN ANATOMICAL PATHOLOGY

CROSS REFERENCE TO RELATED APPLICATIONS

This application is a continuation of U.S. application Ser. No. 11/639,586 filed Dec. 15, 2006 (pending), which claims priority to U.S. Provisional Application No. 60/751,807 filed Dec. 19, 2005, all of which are hereby incorporated by reference.

BACKGROUND

1. Field of the Invention

The methods of the invention are directed generally to the field of anatomical pathology, more specifically to the art of tissue staining. Yet more particularly, the methods demonstrate a novel technique for enhancing workflow through the AP lab by better coordination of information management.

2. Description of Related Art

Traditional manufacturing processes often encompass single skilled operators, high work in process inventories, constant expediting, and production schedule shuffling. These features add limiting effects, such as inefficiency in output, manpower, high work in progress inventories, and assembly line operations. Originally, lean production was implemented in manufacturing or assembly line processes to overcome the problems associated with traditional manufacturing. Lean production was based on the Toyota manufacturing system and typical practices can be found in "The Machine that Changed the World," by James P. Womack, 1991, Harper Collins Publishing Co. The basic philosophy of the lean production system is to manufacture in the most economical way possible. This is accomplished by focusing on meeting customer requirements, such as producing a high-quality product while minimizing wasted resources and time.

The hospital-based Anatomical Pathology ("AP") laboratory has evolved around the individual patient case. That is, each patient will require anywhere from 1 to approximately 20 tests (slides), based on the clinician's initial diagnosis. Therefore, AP labs have evolved a series of "batch"-based processes that reflect this initial workflow model. To accommodate the AP labs, companies have provided workflow solutions that emulate this batch process, and the AP lab has evolved into a series of batch workflow modules. Traditionally, IHC and Special Stains tissue staining was performed manually, and up to about 1991 with the advent of the 320 System from Ventana Medical Systems, Tucson, Ariz., there was no alternative to the tedious manual staining process. The tissue staining process is divided into a series of fundamental steps comprising embedding the tissue in paraffin, sectioning the tissue into thin (4 microns is typical) slices called "sections," mounting the sections on a microscope slide, deparaffinizing the paraffin-embedded tissue sections, changing the hydrophobic environment the tissue then exists in to an aqueous environment via a series of graded xylene/alcohol/water baths, staining the tissue using one of five basic techniques (H&E, Papanicolau stain, IHC, ISH or Special Stains), re-grading the tissue to a hydrophobic environment, and finally coverslipping the tissue for archival purposes. Most of these processes are performed on a "batch" of samples simultaneously for economy of scale. Automated tissue staining can be thought of as a series of automated batch processes that mimics, for the most part, the manual processes.

For example, one of the first steps is embedding the tissue in paraffin so that it can later be manually cut by a microtome into a section. Companies such as Sakura (TISSUE-TEK™), ThermoShandon (EXCELSIOR™), Leica (ASP300™), and Vision Biosytems (PELORIS™) and others provide tissue processors that process tissue blocks by the hundreds, but all in batch mode. There is one new entrant that purports to continuously process tissue, the Sakura Xpress™. Also, most Hematoxylin & Eosin primary staining systems are also batch in that they stain baskets or trays of slides in large numbers simultaneously. See, e.g., the Leica XL Stainer, the Sakura DRS-60, etc.

A fundamental concern in today's AP lab is sample tracking. Hospitals are continuously challenged by the size and complexity of testing requirements, as clinicians and primary care professionals demand more and faster turn-around times. Opposed to this pressure for more/better/faster is the need to unambiguously track samples so that mix-ups and errors do not occur. The computer is ideally situated to do this, and so hospital information systems have been developed to track every hospital-based activity from admissions to testing. In addition, systems vendors have also designed Laboratory Information Systems ("LIS") that are a part of or integrate with the Hospital Information System ("HIS") so that labs can manage their unique requirements while remaining in contact with their customers. A typical LIS is designed and sold by Cerner as the PathNet® family of laboratory information solutions (Cerner Corp., Kansas City, Kans.).

A typical workflow in today's AP lab is shown in FIG. 1. It is a mix of manual and automated batch processes that is ripe for additional improvement. A fundamental issue remaining to be resolved is the lack of a complete information tracking solution for the entire tissue staining process.

SUMMARY OF THE INVENTION

An embodiment of the method of the invention is a method of automating information flow in a laboratory performing tissue staining comprising positioning a networked label printer adjacent to a cutting station, the printer configured to access patient data directly or indirectly from the hospital LIS, the printer being configured with a data element scanner in electronic communication with said printer; inputting data from a tissue cassette-associated data element at said printer, whereby inputting data comprises reading the data from the cassette-associated data element and uploading the cassette data to the LIS; identifying the corresponding test protocol identifier and then downloading the test protocol data to the printer; printing information on labels corresponding to each test specified in the LIS for the patient; attaching a single label to each slide; and cutting a tissue section for each labeled slide and mounting the section on the slide.

Another embodiment of the invention is a method of coordinating tissue sample information in a laboratory staining process, comprising the steps of identifying a tissue cassette comprising a tissue sample to be tested to a LIS-networked machine-vision system; transferring machine-readable identifying information associated with the tissue sample to the LIS; accessing test instructions for the tissue sample via the LIS, the test instructions determining the sections to be cut and the protocols to be performed on the respective sections; instructing a label printer to print the required number of labels encoding the protocols to be performed on the corresponding tissue sections; printing a slide label encoding each protocol to be performed on the corresponding tissue section; attaching the slide label to a slide; placing at least one tissue section on the labeled slide; and staining the tissue section(s) on the slide in accordance with the protocol identified on the corresponding slide label.

DETAILED DESCRIPTION OF THE INVENTION

A. Introduction

Figure 1:
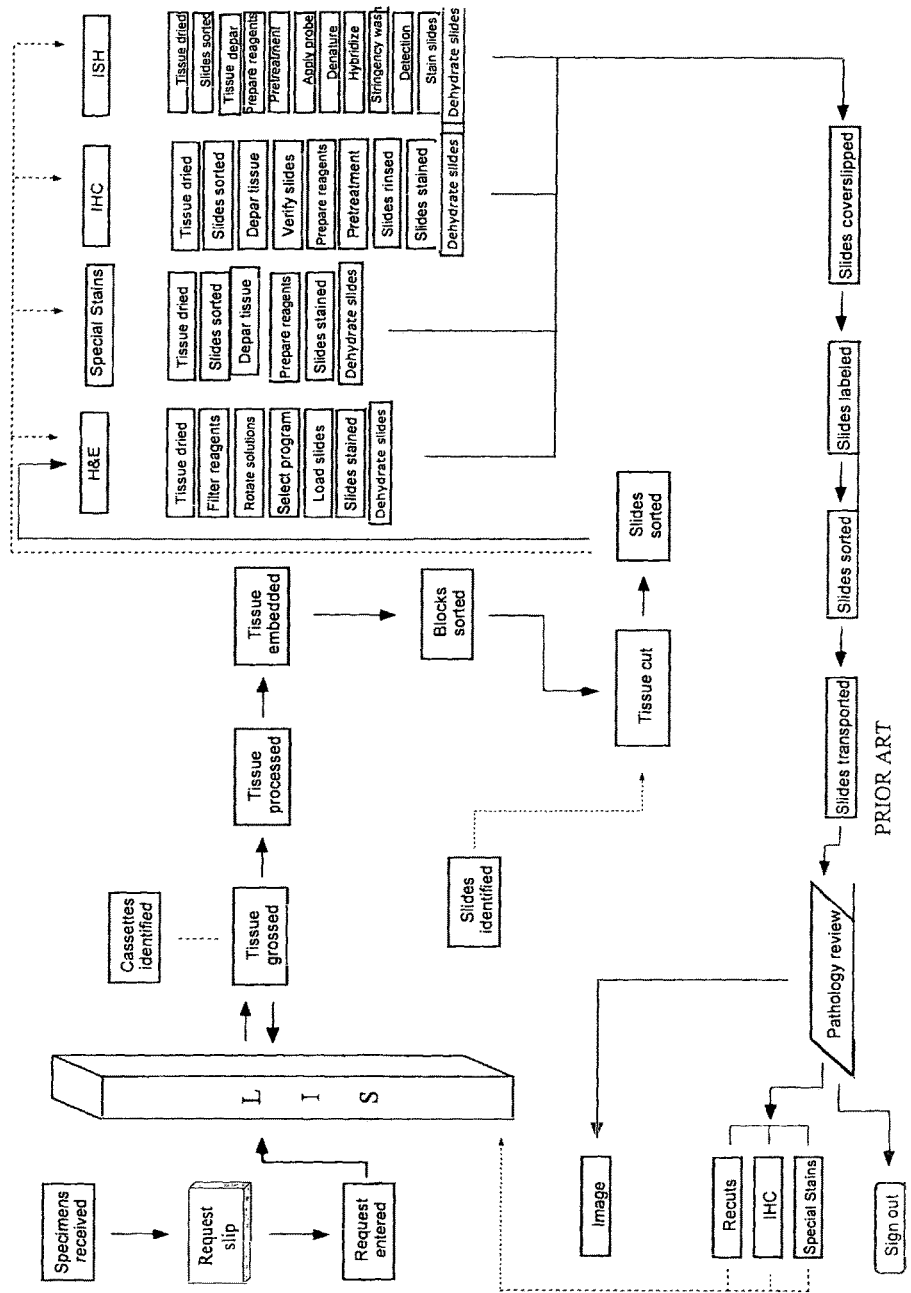
FIG. 1 is a flow diagram depicting the histology value stream map for a tissue sample traveling through its various processes from receiving to sign-out.

Lean methodology comprises 5 basic steps: 1) observe the process you wish to model, 2) define that process, 3) define opportunities within the existing process, 4) develop improvement opportunities, and 5) implement and sustain the improvements. Lean principles as applied to the Anatomical Pathology lab suggest that developing a map of the existing process is a recommended starting point. In FIG. 1 is shown a Histology Process Map, which is a visualization of one particular histology production path, including both materials and information. At the left side of the figure the sample is first received ("Specimens Received"), then a Request Slip is generated for the tests to be performed, which is entered via the hospital's Lab Information System ("LIS"). Typically the LIS is a networked software enterprise that links requesters and providers with test request and test status and result information. The system normally is all-inclusive: anyone in the hospital who needs to request or process requests for testing may have access to it. It stores test requests and test data for patients within the hospital, and submitted from outside on an out-patient basis too. The LIS will have a database for tracking the test for each patient having tests performed. The LIS will assign a case number to the patient and correlate the patient's case no. with data such as the treating physician, other physicians involved in the case, inpatient/outpatient status, insurance information, requested tests, status of tests, results of tests, etc.

The general AP lab process is described herein, but includes many steps for each of the general processes described. Accessioning is the first step in tracking the sample through the use of the LIS. Sample identity, test requests, case no., etc. are assigned and/or logged into the LIS during accessioning. Some AP labs assign an "accession number" in addition, which is a unique numbering system for the AP lab only. The data typically includes the case number which is usually the unique identifier assigned by the hospital LIS to identify the patient. The LIS database will have further data linked to the case number which will define the tests to be performed in the AP lab. Typically such test data includes the type of staining tests such as a primary stain ("H&E") and/or a secondary stain ("Special Stains/IHC/ISH"). The primary stain is normally a Hematoxylin and Eosin combination stain. Secondary stains include a "Special Stain," an Immunohistochemical ("IHC") stain, or an in situ hybridization ("ISH") stain. Pap stains are yet another type of specialized stain.

Still referring to FIG. 1, once cassettes have been identified and entered into the LIS, they then enter the grossing station. This is where the "gross" tissue is prepared for all further analytical treatment. The appropriate tissue samples are placed in cassettes, which are small, perforated plastic containers having hinged doors for holding tissue samples for subsequent chemical processing and paraffin infiltration. The cassettes must have some form of data element written or encoded upon them in either indelible ink, or in a machine-readable label such as a bar code or RFID. The data element is necessary to track the sample while in the cassette. The samples in the cassettes are then submitted to tissue processing and embedding in paraffin. Tissue processing typically results in the samples being immersed in multiple baths of progressively more concentrated ethanol to dehydrate the tissue, followed by a clearing agent such as chloroform, xylene or Histoclear™, and finally hot molten paraffin wax (infiltration). During this 4 hour process, paraffin wax will replace the water: soft, moist tissues are turned into a hard paraffin block, which is then placed in another cassette containing more molten wax (embedding) and allowed to cool and harden. The resulting tissue sample has its water replaced with paraffin, and is hard enough for cutting into thin, essentially transparent slices or "sections" of the tissue.

In the sectioning process, due to the fragility of the sections, they are first manually cut and then floated onto the surface of a water bath, where they flatten out and float. Each section is then picked up from beneath by raising a slide below a floating section so that the section settles onto the slide surface. After drying and baking the sections onto the slide they are then ready for the staining process. However, the paraffin-embedded sections must first be deparaffinized, and then the paraffin solvent must be exchanged (again) with successive ethanol:water solutions until the tissue is again steeped in an aqueous environment. Most stains are water-based but in any event they selectively highlight tissue structures to reveal the morphology of the tissue sample. Morphology is the key to determining whether the sample is normal or not. Normal morphology indicates no further testing is necessary, while suspect morphology may prompt recuts for additional primary and/or secondary staining. After staining, the slides are dehydrated again to allow for archiving using glass coverplates, which are glued onto the tissue section using a non-aqueous glue to create a permanent, coverslipped slide. Lastly, the slides may be permanently labeled, sorted and transported in a group arranged by patient or case no. to the Pathologist for review and analysis. At this point, the Pathologist will determine whether imaging, additional staining, or signing out is the next step.

Tissue staining may also be performed on intact cells, and when done so is termed "Cytology." For example, cervical samples are taken from the cervical area by a wash process whereby the surface of the cervix is brushed and washed, and the washed cells are collected in a specially formulated preservative solution. The cells are then filtered onto a charged glass slide where they adhere for further staining operations. For purposes of the present invention, whether the methods of the invention are performed on tissue samples or cells is irrelevant. One system that automates the filtering and applying steps is sold by TriPath, Inc. (Burlington, N.C.).

It should be understood that this basic flow has existed for the recent past, and all processes until the last 10 years or so were performed manually. The typical Histology lab may employ several individuals to perform all of these steps, who may collectively process up to 500 slides a day, and so the tissue may shuttle through a chain of custody during its stay in the AP lab. With the advent of automation and lean systems design, the paradigm for the AP lab is evolving quickly. Clearly, with all of the manipulations of the tissue that occur during this process, accurate tracking of the samples has become of extreme importance.

B. Definitions

The following terms are intended to have the indicated meanings denoted below as used in the specification and claims.

The term "networked label printer" means a label printer that is connected to a laboratory information system or network. "Networked" means in general that an electronic device is connected to an electronic network capable of communicating both data and command information. In the present context the networked label printer receives data that is to be printed on the slide labels. The label printer may also send signals to the network regarding its status for readiness for accepting instructions to print, status of the print jobs in its print queue, printed labels awaiting affixation to slides, etc.

The terms "label printer" and "labels" includes standard slide label printing devices such as the EBAR™ printer (Ventana, Tucson, Ariz.) and the labels that go with it. The EBAR is not network-ready, but a network-ready label printer is sourced through General Data (Cleveland, Ohio), called the SATO CT410DT thermal printer, and is used in conjunction with the StainerShield™ slide labels and Ultra-Label™ Gold v. 7 software. Slide labels need to fit the frosted end of the slide and also need to withstand the chemical processing steps they may be subjected to, including contact with solvents such as xylene and alcohol. In addition, the term "printer" may also apply to a device that prints directly to the slide such as a slide printer or slide etcher. These devices may etch via laser or print the bar code directly to the slide in indelible ink, thus obviating the need for a separate label. An example of such a device is the Leica IPS, (Leica Microsystems AG, Wetzlar, Germany) which also prints on tissue cassettes.

The term "patient data" includes data stored or accessible by the LIS that is uniquely associated with a patient. Typically this data includes the patient's name, case number, the tests to be performed on the patient's tissue sample, the protocols and their respective identification numbers that correlate to the test, the date the tissue was entered into the LIS, the doctors associated with the patient, etc.

The term "cutting station" means the area dedicated to sectioning tissue in a tissue cassette using a microtome or similar device. The cutting station is the workplace area where the tissue cassette is placed into a microtome for subsequent cutting operations, usually performed manually by a histology technician. The sections are approximately 3-6 microns thick, and are "floated" onto a water bath where they then are picked up on a slide. The cutting station includes a microtome with its water bath, and may also include a machine-vision capable scanner capable of reading information from e.g. a barcode.

The term "LIS" is shorthand for "Laboratory Information System." A LIS is commonly understood to be a software-driven electronic network for connecting lab instruments and computers so that at a minimum their statuses may be monitored through one or more centrally-located computers. Elements of the software allow common control and communication amongst a group of instruments that share a common networking protocol. One such protocol is the HL-7 protocol. HL-7 is an ANSI standard for healthcare specific data exchange between computer applications. HL-7 stands for "Health Level 7", which refers to the top layer (Level 7) of the Open Systems Interconnection (OSI) layer protocol for the health environment. Most new lab instruments have now adopted this protocol. A typical LIS is designed and sold by Cerner as the PathNet® family of laboratory information solutions (Cerner Corp., Kansas City, Kans.). Other LIS's are the Impac (Tamtron), and MediTech's LIS-Magic.

The term "data element" means a device for capturing/storing data in a machine or human-readable format. Examples include a slide label containing both alphanumeric information such as the case no. and a barcode for a barcode scanner to read. A typical data element is a barcode label, although others may include a Radio Frequency Identification Device ("RFID"), a magnetic stripe with magnetically-encoded information contained with it such as found on credit cards, or optically-encoded text information that may be read by a digital camera and translated via Optical Character Recognition (OCR) software. Barcodes may also include fully optically-readable devices such as optically-encoded elements 1-D and 2-D barcodes, data matrixes, and data glyphs. Alphanumeric characters on a slide label may also be data elements. Alphanumeric characters may be scanned by a digital camera, the text decoded via OCR software, and the resulting information transferred or stored for later use.

The term "data element scanner" includes any machine vision system configured to read the encoded information from the data element as defined above. Typical scanners include RFID readers, barcode scanners, magnetic strip readers, digital cameras, etc.

The term "in electronic communication" means that the system being referred to is electrically connected, either via hard connection (e.g. copper wiring, fiber optic cables, etc.) or wirelessly through a wireless link, to another system for which communication is desired, and both can either send and/or receive signals from the other.

The term "tissue cassette" is a common descriptor for a tissue sample case which functions to position and contain the tissue sample for embedding in paraffin. After embedding, it continues to be used to position the sample for subsequent cutting in the microtome. A tissue cassette needs to have basic identifying information associated with it because the samples are usually loaded in batches of several hundred to the embedder. Thus, each cassette must have at least one unique identifier such as a cassette number, case number, accession no., or a combination of the them in order for the lab to track the tissue sample within. Typically a cassette has the accession or case no. information encoded in a barcode, or alphanumeric text is written in indelible ink. For purposes of the present inventive methods, either come within the scope of the invention.

The term "cassette data" refers to the unique identifying number for the cassette, if any. Cassette data would be used by the histology lab to track cassettes. The case number may also be included in the cassette data.

The term "identifying" as used in the phrase "identifying the corresponding patient test protocol data" means that the LIS or an intermediary software application associates the cassette data with the tests to be run on that specific sample, and then the LIS or intermediary will send instructions to the printer to print the required labels, based on the number and types of tests specified in the LIS or intermediary.

The term "machine-vision system" means any machine-based system having the capacity to translate and/or communicate information encoded in the electromagnetic spectrum into information cognizable by a machine. Common machine-vision systems available today include camera-based systems, the cameras designed to detect information from the infrared, ultraviolet, x-ray, and visible portions, to name a few. Other machine-vision systems may read and send information in the radio portion of the electromagnetic spectrum such as RFIDs, mentioned previously. Any machine-vision system now know or hereafter developed comes within the scope of the present invention.

The term "machine vision identifying information associated with a tissue sample" means the encoded information attached to or associated with the tissue sample, as for example, a barcode on a slide having a tissue specimen thereon, or an RFID attached to or embedded in a tissue cassette holding a tissue sample. However, the identifying information may also be indirectly associated with the cassette.

The term "test instructions" are those tests that have been ordered by the clinician for the respective patient. These instructions normally indicate the type and number of tests to be run. Test instructions may specify a primary stain such as an H&E (Hematoxylin and Eosin) stain, any number of secondary stains such as an Immunohistochemical stain utilizing antibodies specific for disease markers, a in situ hybridization (DNA probe) stain, or a Special Stain (a purely chemical stain). In addition, control tests may also be specified by the test instructions.

The term "test protocol identifier" is the unique number used to associate a protocol with its individual steps or the recipe for the protocol. For a staining protocol, each protocol includes a number of staining steps needed to perform the entire staining process on that individual tissue section. Other protocols may be specific for deparaffinization, antigen retrieval, baking, and other processes automated by a staining system. The test protocol identifier is typically encoded in a machine-readable identifier such as barcode label so that when an automated staining system reads the slide label, it then uses the protocol identifier to look up in a protocol table the requisite steps for performing the staining operation. A full run will require hundreds and perhaps thousands of individual steps to complete the testing for the numerous samples being processed. For example, the BenchMark™ XT system (Ventana, Tucson, Ariz.) has a 30-slide capacity, which means 30 tests may be run simultaneously, each test having from 50 to 100 individual steps.

The term "case no." is the identifier given by the hospital to the individual patient sample. It is the key to maintaining the confidentiality of the patient, yet allows the hospital staff to track and complete their tasks without compromising the patient's identity.

"VIP/VLM" refers to the Ventana Interface Point/Ventana Lab Manager software embedded in the NexES v. 10.1 software (Ventana, Tucson, Ariz.). The VIP serves as the interface between the LIS and the VLM. The VLM is the managing software that facilitates replication of data between Ventana automated staining systems, thereby allowing them to share reagents and status data so that staining operations may be optimized in a lab running multiple Ventana staining instruments. A fuller discussion is contained in U.S. patent application Ser. No. 11/032,324 filed Jan. 10, 2005, incorporated herein by reference.

C. Description of Embodiments of the Invention

An embodiment of the method of the invention is a method of automating information flow in a laboratory performing tissue staining comprising the following steps. First, positioning a networked label printer adjacent to a cutting station, the printer configured to access patient data directly or indirectly from the hospital LIS, the printer being configured with a data element scanner in electronic communication with said printer. It is efficient from a lean systems perspective to position the label printer next to the cutting station because the LIS will send print commands for slide labels that correspond to cassettes located at the same cutting station. Thus, it is more efficient for the cutter to stay at the cutting station and not to have to get up and locate the labels at a label printer located some distance away.

The next step involves inputting data from a tissue cassette-associated data element at the label printer, whereby inputting data comprises reading the data from the cassette-associated data element and uploading the cassette data to the LIS. The data element may be, e.g., a barcode label, and the cassette data encoded within the barcode may be a unique identification code for the cassette. That code would already be assigned during accessioning, and the LIS correlates the tests to be run with that cassette code. In the case of a barcode, the step of reading the data may be accomplished simply by scanning the cassette bar code with a barcode scanner. The barcode scanner may be standalone, or alternatively may be built into the microtome or label printer. It is not important to which device it is attached, if any. The barcode scanner may be a wireless hand-held scanner. If the data element is not a barcode but is an RFID for example, then the AP lab may have a RFID lab network tracking the samples at all times. Inputting data from an RFID-equipped cassette may be as simple as "wanding" the cassette within the reading range of the RFID reader. The RFID reader would detect the presence of the cassette and register it with the LIS as ready for slide label printing. Alternatively, the cassette data may be manually entered into the labeling software GUI if for some reason the cassette data cannot be read by the barcode scanner. Reading and uploading the data would then be accomplished manually, and comes within the scope of the inventive methods of the invention.

The next step is identifying the corresponding patient test protocol data and then downloading the test protocol data to the printer to be printed on labels. As mentioned above, the LIS will already have entered into it a list of tests to be run on the specific sample that corresponds to the cassette data. The LIS or an intermediary software application such as the Ventana Lab Manager ("VLM," Ventana, Tucson, Ariz.) may correlate the cassette data with the sample and tests that have been ordered by looking up the case no. data in the LIS/VLM. The case number will dictate the number of sections to be cut, which in turn determines the number of labels required. Specific protocol identifiers are downloaded to the label printer, where each label will have them printed on it. The labels are used by the automated stainer in the next phase of the staining process. The protocol identifiers are read by the automated staining system, correlated with the correct series of staining steps (a staining "protocol") and the run is performed accordingly. Each label may also contain human-readable characters describing various important information such as case no., stain type, etc.

The next step comprises printing information on labels corresponding to each test specified in the LIS for the patient and attaching a single label to each slide. As previously described, after the LIS identifies the test protocol data from reading the cassette, the protocol identifiers are sent to the label printer for printing. Slide labels are printed and the histotechnician places them on the frosted end of the slide. There are only two possibilities at this point for slide labeling: the slide is labeled before the sample is placed on it, or the slide is labeled afterwards. The methods of the present invention contemplate either situation. The labeling step completes the transfer of information from the cassette to the slide, and is an important step ensuring that the sections have the same identifying information as the cassette.

If the test ordered is an IHC, Special Stains or an ISH test, then a positive control slide will be needed. The positive control slide has a positive sample on it, and information identifying it as such. After the cassette has been identified to the LIS, the LIS patient information will already specify a positive control, and a slide label will be printed that contains information identifying both the sample and the positive control. This new label will be overlaid on the original positive control slide.

The final steps are cutting a tissue section for each labeled slide and mounting the section on the slide. Normally, the technician will print all the labels, then label the slides, and park the labeled slides next to the water bath. The technician will then cut a series of sections, one per slide, and leave them floating for pickup. Then the technician will pick up one section per slide (H&E) or additional sections on additional slides if a secondary stain (IHC/SS/ISH), and place the slide on a rack for the baking step. Tithe technician is labeling first and applying tissue second, then there should be a minimum possibility of error at this stage. However, if the technician is applying tissue first and labeling second, then he must be sure the block in the microtome corresponds to the slide labels. Otherwise, there will be unlabeled slides with tissue sections on them in the cutting area, raising question about what their identity is.

A slightly different process applies when the stain is an IHC stain. As previously mentioned, a positive control slide must be used. A positive control slide already has a tissue section adhered to it that will be positive, that is, it will react with the stain to highlight the presence of the biochemical marker being tested for. For instance, if a test for ER (Estrogen Receptor) has been ordered, then the sample will be adhered to an ER positive control slide, which comes with an ER-positive "control" tissue on it. The result is that there will be two sections on the slide, one a known positive, and the other the test sample. If all automated staining functions are working correctly, then in the event of a negative sample at least the positive control will stain. If both tissues stain positive, then the sample is truly positive. A positive control slide contains information providing traceability and/or some indication of what the test is. For example, in the above ER situation, the slide will have a label or penciled information which contains "ER positive" and/or a traceability number somewhere on it. In order to ensure the cassette/sample data gets matched to the correct slide, the positive control slide label will have to be over labeled with a new label containing the previous information (e.g. "ER positive") and the new sample data. For primary staining a "batch control" may be used, which is a single control for an entire batch of slides, to ensure the staining system is working properly. Another embodiment of the invention is directed to a method of coordinating tissue sample information in a laboratory staining process comprising the steps of identifying a tissue cassette comprising a tissue sample to be tested to a LIS-networked machine-vision system. The machine-vision system is commonly described as a machine, instrument or computer enabled with a remote information reading capability. Common examples of such machine-vision systems are robotic cameras used on assembly lines to identify parts and tools, barcode scanners such as supermarket checkout scanners, RFID-enabled systems which have the additional capability of writing to the RFID on the product being tracked, etc. These are examples of optical and radio-frequency devices.

The next step is transferring machine-readable identifying information associated with the tissue sample to the LIS. The identifying information associated with the tissue sample is commonly the cassette identifier or case number. In either event, it may be printed or etched onto the cassette surface by a printer or laser-based etcher so as to create an indelible pattern readable by a human and/or machine. For example, the act of transferring the information is met by the scanning process, for a barcode. The barcode scanner will read the barcode information and then transmit it to the LIS or middleware solution such as the VLM, mentioned previously.

The next step is accessing test instructions for the tissue sample via the LIS, the test instructions determining the sections to be cut and the protocols to be performed on the respective sections. As mentioned above, the LIS will already have entered into it a list of tests to be run on the specific sample that corresponds to the cassette data. The LIS or an intermediary software application such as the Ventana Lab Manager ("VLM," Ventana, Tucson, Ariz.) correlates the cassette data with the sample and tests that have been ordered by looking up the case no. data in the UIS/VLM. For example, if the test instructions in the LIS say "ER" for this case no., then the LIS will formulate the command to print two labels, the first having the ER protocol identifier and the case no., and the second label having the ER positive control tissue protocol identifier and case no. on it. Although the control test may not be specified in the LIS, the LIS should be programmed so that by default if certain tests are ordered, then the requisite control will also be added to the list of tests to be run.

The LIS or VIP/VLM will instruct a label printer to print the required number of labels encoding the protocols to be performed on the corresponding tissue sections. It should be known to one of ordinary skill that a slide printer may also be used for this function. A slide printer directly encodes the information onto the surface of the glass slide, eliminating the need for a separate labeling step. An example of a slide printer is the Leica IPC, (Leica Microsystems AG, Wetzlar, Germany).

The last steps of the process include printing a slide label encoding each protocol to be performed on the corresponding tissue section; attaching the slide label to a slide; placing at least one tissue section on the labeled slide; and staining the tissue section(s) on the slide in accordance with the protocol identified on the corresponding slide label.

More than one section may be placed on a slide, including in some embodiments one or more control tissue sections.

The following examples are illustrations of the embodiments of the inventions discussed herein, and should not be applied so as to limit the appended claims in any manner.

D. Examples

Figure 2:
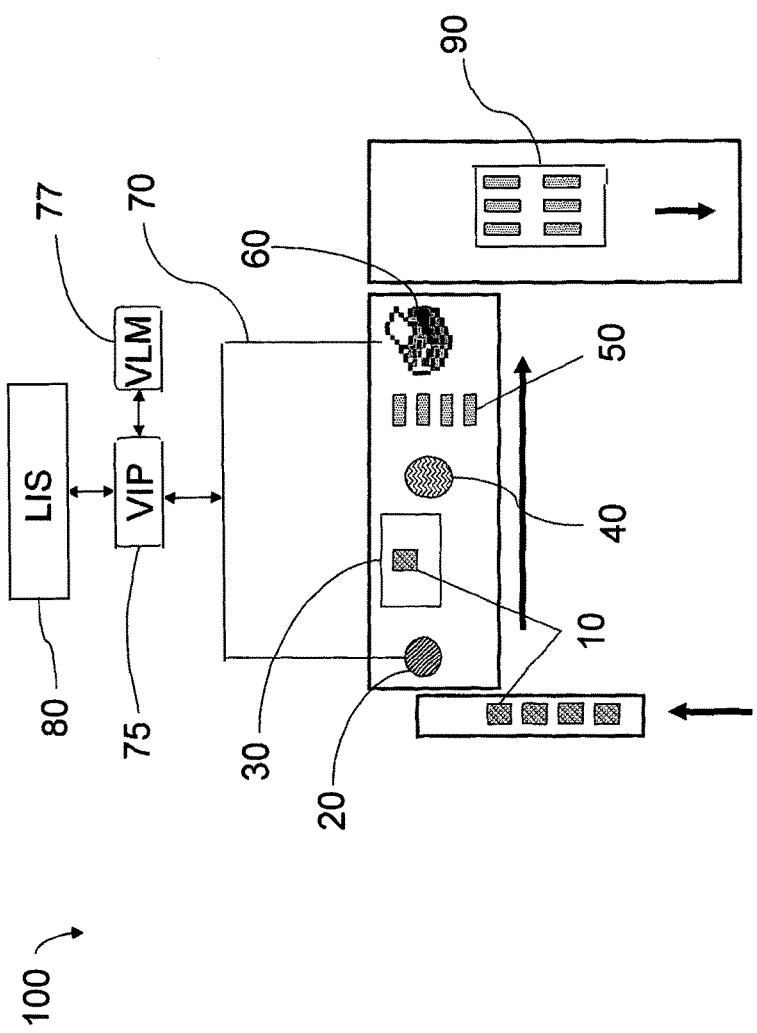
FIG. 2 is a picture-diagram of an embodiment of the present invention showing the method as practiced in one scenario.

FIG. 2 is a picture-diagram of one embodiment of the invention. It depicts the basic flow of a tissue cassette coming from Embedding to the Cutting Station. Cassettes 10 having paraffin blocks containing patient samples embedded in paraffin are located in a queue waiting to be scanned in at the scanner 20. Scanner 20 may be a barcode reader, an RFID antenna, a magnetic stripe reader, an imaging system using a digital camera or any similar machine-readable technology, depending of course on the technology adopted by the AP lab. Assuming for purposes of illustration only the scanner is a barcode scanner, at the scanner 20 the technician will scan the cassette and the scanner will send the data to the laboratory network or data bus 70 for further processing by the LIS 80 via the VIP 75. The lab may utilize an intermediary software solution such as the Ventana Interface Point/Ventana Lab Manager ("VIP/VLM") software/hardware 75/77 to provide an interface between a network of Ventana instruments and the AP lab's LIS. The VIP/VLM is described in more detail in co-pending U.S. patent application Ser. No. 11/032,324 (Showalter, et al.) filed Jan. 10, 2005, incorporated herein by reference in its entirety. LIS 80 is described in more detail infra in FIG. 3. Microtome 30 has mounted in its block a cassette 10, which is to be cut by a technician. Sections (not shown) are floated onto water batch 40 and await pick-up onto slides 50. Slides 50 may be labeled prior to pickup, or may be labeled immediately after pickup. If the test is an to IHC test, then the slide may be a positive control slide, in which case it will need to be re-labeled. In either event, label printer 60 prints slide labels having barcoded information readable by the stainer. The slide labels will at least contain the case no. It will generally contain the stain protocol identifier as well. After the tissue has been picked up and the slide labeled, the slide will be placed on a tray 90 that will then be placed into an oven for a short baking cycle to adhere the tissue to the slide for the subsequent tissue staining processes.

Figure 3:
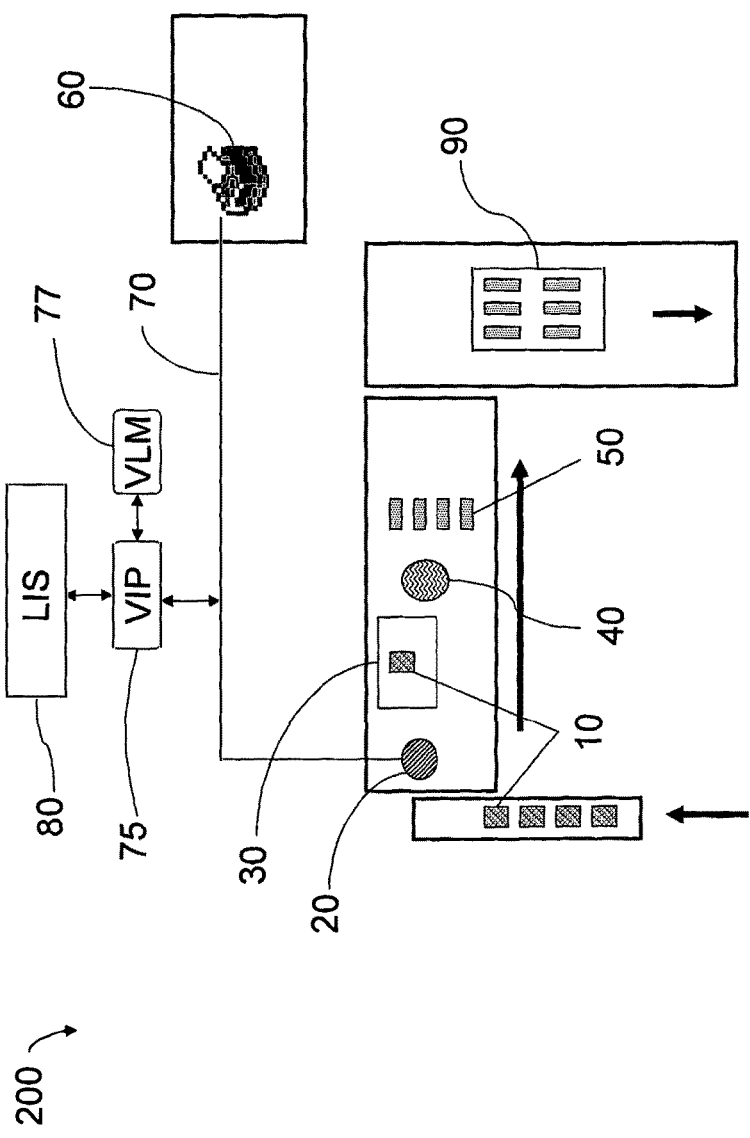
FIG. 3 is a picture-diagram of an alternative embodiment of the invention.

FIG. 3 illustrates an alternative embodiment. It differs from the embodiment of FIG. 2 in that the label printer 60 may be a shared lab resource, and thus may be located distal to the cutting station. Label printer 60 is still networked to the VIP/VLM and in electronic communication with the LIS, but a separate printer is not located at each cutting station. Each cutting technician will therefore have to go to the labels, or the labels will have to be brought to them.

Figure 4:
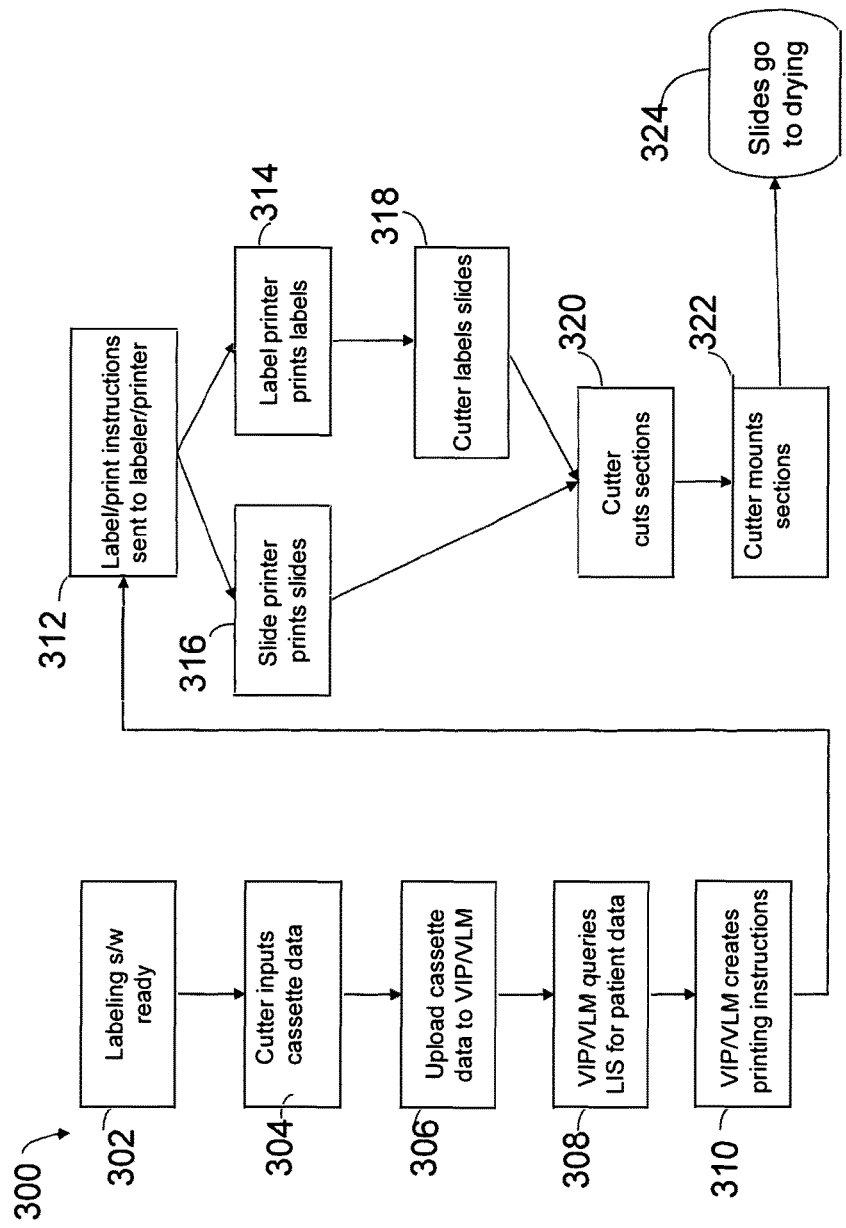
FIG. 4 is a diagram showing the function blocks of the LIS.

FIG. 4 is a flow diagram showing the steps of a method of the invention. In step 302, the labeling software graphical user interface ("GUI") is open and a data input screen allows the histotechnician to input cassette data, or monitor the automated scanning of the cassette data into the VIP/VLM. In step 304, the histotechnician responsible for cutting sections ("Cutter") inputs the cassette data either by scanning the cassette, or by manually inputting the cassette identifying information. Preferably it is automated so as to reduce data entry errors. In step 306, the cassette identifying information is sent or made available to the VIP/VLM. Once the VIP/VLM records that it has a new cassette at the cutting station, it queries the LIS in step 308 for the corresponding patient data, including the tests to be performed. In step 310, the VIP/VLM will format the proper test instructions for printing on a slide label. Alternatively, if a slide printer is being used instead of a slide labeler, the VIP/VLM will formulate the instructions for the slide printing process. In step 312, the labeling or printing instructions are sent to the label printer or slide printer, as the case may be. At this point the diagram diverges to illustrate the two potential paths. If slides are to be printed, processing continues with step 316 where the slide printer prints the slides. If the system includes a labeler steps 314 and 318 are performed. The extra step of labeling is performed by the Cutter in step 318.

Next, in step 320, the Cutter cuts the sections and floats them onto the water bath. Finally, in step 322, the Cutter mounts the sections on the labeled or printed slide and they are then ready to go to the drying (or baking) step 324.

Figure 5:
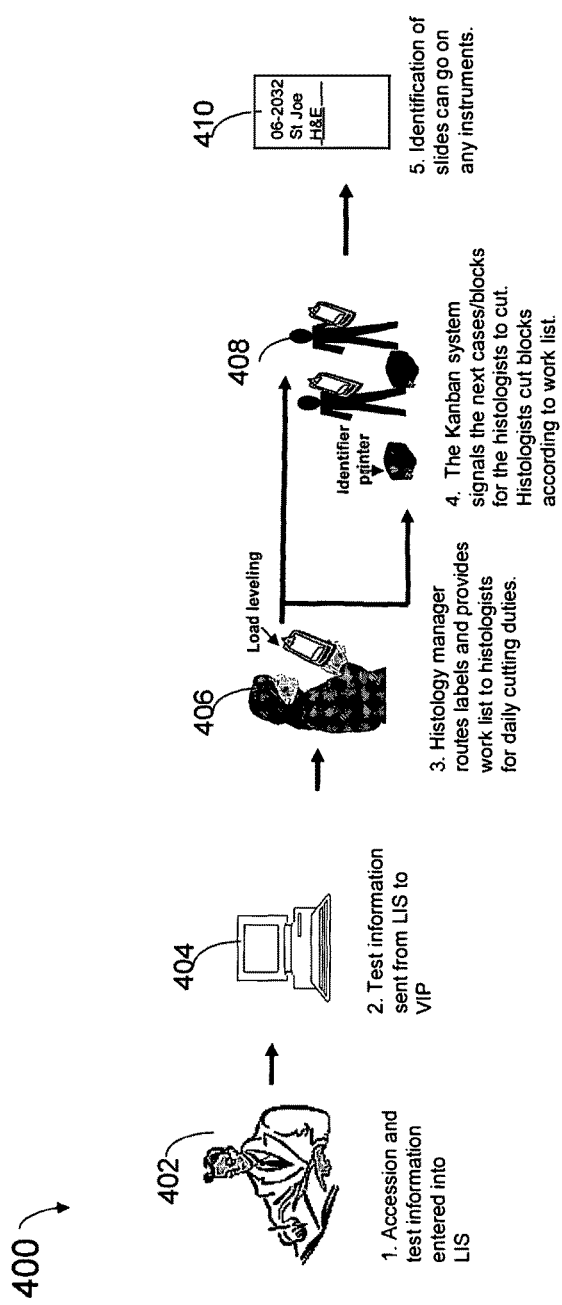
FIG. 5 is a flow diagram illustrating processing steps in one embodiment of the techniques herein.

FIG. 5 is a flow diagram illustrating processing steps in yet another embodiment of the techniques utilizing the principles of JIT (Just in Time) manufacturing for Histology. In step 402, the accession and test information is entered into the LIS. In step 404, test information is sent from the LIS to the VIP/VLM. Processing associated with step 402 that may be performed in an embodiment is described elsewhere herein, for example, in connection with steps from FIG. 3. In step 406, the Histology Manager may intervene to set work priorities for the cutters. The foregoing may be termed "load leveling" and involves distributing the appropriate activities to the cutters so as to ensure no work bottlenecks occur. The introduction of "level loading" after the information is sent from the LIS allows management to balance the distribution of blocks to individual cutters thereby better managing lab productivity. The distribution of work to the cutters as performed in step 406 may be performed by the Histology Manager considering any one or more different factors. For example, the work distribution may be based on the availability and current load of each cutter, any cutting expertise or specialty of each cutter for the various types of tissue samples, and the like. After the load leveling step 406, the printer prints instructions (typically case number or name) in step 408 to signal to each cutter which is/are the next case(s) or block(s) to cut. In other words, the action of printing drives or controls the cutting process in that printing serves as a signal to the cutter of when to cut a next section and from which sample. The foregoing refers to application of the Kanban System and techniques. "Kanban" is a Japanese term that means "signal." In JIT manufacturing, the term Kanban may be used to denote a stocking system that uses signals to make production systems respond to real needs and not predictions and forecasts. Introducing the foregoing principles and techniques reduces the overproduction of blocks/slides and eliminate mistakes.

It should be noted that the load leveling step 406 may be performed at various points prior to the printing. For example, as described herein with reference to FIG. 3, the VIP/VLM creates the printing instructions in step 310 and then sends the printing instructions to the label or printer in step 312. In one embodiment, the load leveling may be performed prior to the VIP/VLM sending the print instructions to the labeler or printer, such as after step 310. In another embodiment, the load leveling may be alternatively performed after the print instructions are sent to the printer in step 312 but prior to printing in either of steps 314 or 316. In yet another embodiment, the load leveling may be performed after the VIP/VLM receives the test information from the LIS (e.g., step 308) but prior to creating the printing instructions in step 310.

The step of load leveling as described herein may be performed by the histology manager or other appropriate individual using any one or more manual and/or automated techniques. For example, in one embodiment, the distribution may be performed by the histology manager visually inspecting and/or verbally inquiring of individual cutters regarding their capacity. In another embodiment, software may be used to track and monitor the current allocations, workload, and/or performance aspects of the various cutting stations and used in connection with determining the distribution of additional samples. The foregoing are just examples of different manual and/or automated techniques that may be utilized in an embodiment.

It will be understood that various modifications may be made to the embodiments disclosed herein. Therefore, the above description should not be construed as limiting, but merely as exemplifications of preferred embodiments. Those skilled in the art will envision other modifications that come within the scope and spirit of the claims appended hereto. All patents and references cited herein are explicitly incorporated by reference in their entirety.

We claim:

1. A method of automating information associated with tissue samples to be stained in a laboratory comprising:

positioning a networked label printer adjacent to a cutting station, said printer configured to access patient data directly or indirectly from a laboratory information system (LIS), said printer being configured with a data element scanner in electronic communication with said printer;

reading, using the data element scanner, cassette data from a plurality of cassette-associated data elements of a plurality of tissue cassettes comprising a plurality of tissue samples to be tested;

uploading said cassette data to the LIS, said cassette data identifying the plurality of tissue cassettes;

identifying, in a database of the LIS using the cassette data, one or more test protocol identifiers for testing to be performed on the plurality of tissue samples for at least one patient;

downloading said test protocol identifiers to said printer;

printing information, including the test protocol identifiers, on labels corresponding to tests specified by the LIS for the at least one patient, wherein an order in which said printing of labels is performed for the plurality of tissue samples indicates the order in which each of said plurality of tissue samples is cut into tissue sections;

responsive to printing labels for a particular one of the plurality of tissue samples for a particular patient, signaling to the cutting station to cut said particular one tissue sample so that the order in which labels are printed for the plurality of tissue samples drives or controls the order in which the plurality of tissue samples are cut into tissue sections, wherein an action of printing serves as a signal to the cutting station for when to cut a next tissue section and from which of the plurality of tissue samples to cut the next tissue section;

attaching a single label to each of a plurality of slides;

cutting and mounting at least one tissue section on each labeled slide; and using, by an automated staining system, the labels in a staining process, wherein the test protocol identifiers on the labels are read by the automated staining system and correlated with a correct series of staining steps performed accordingly.

2. The method of claim 1, wherein said printer is networked to the LIS using the HL-7 (Health Level 7) protocol.

3. The method of claim 2, wherein said patient data includes any of: a case number uniquely associated with each of the at least one patient, and the test protocol identifiers corresponding to the tests ordered for the at least one patient, wherein each test protocol identifier comprises an identification number that uniquely identifies a test protocol to be performed on a slide.

4. The method of claim 3, wherein each of said plurality of cassette-associated data elements comprises a barcode and wherein said data element scanner comprises a barcode reader.

5. The method of claim 3, wherein each of said plurality of cassette-associated data elements comprises a RFID (radio frequency identification device) and wherein said data element scanner comprises a RFID reader.

6. The method of claim 1, wherein said information printed on each of the labels comprises machine readable information.

7. The method of claim 6, wherein said machine readable information comprises a bar code.

8. The method of claim 6, wherein said machine readable information includes information encoded on a RFID (radio frequency identification device).

9. The method of claim 1, wherein said label printed on each of the labels comprises both human-readable information and machine-readable information.

10. The method of claim 1, wherein reading cassette data comprises scanning the plurality of tissue cassette-associated data elements using a scanner.

11. The method of claim 1, further comprising: prior to said printing, performing load leveling to distribute the plurality of tissue samples for cutting.

12. The method of claim 11, wherein said load leveling is performed to distribute the plurality of tissue samples to a plurality of cutting stations in accordance with at least one of: work load of each of said plurality of cutting stations and cutting expertise.

13. The method of claim 1, further comprising:
    performing load leveling to distribute the plurality of tissue samples for cutting, wherein said step of performing load leveling is performed after downloading said test protocol data to said printer.

14. The method of claim 1, further comprising:
    performing load leveling to distribute the plurality of tissue samples for cutting, wherein said step of performing load leveling is performed prior to downloading said test protocol identifiers to said printer.

* * * * *